(12) United States Patent
Callegaro et al.

(10) Patent No.: US 6,172,219 B1
(45) Date of Patent: Jan. 9, 2001

(54) AUTO-CROSS-LINKED GELLAN GUM

(75) Inventors: Lanfranco Callegaro, Padua; Filippo Biviano, Abano Terme; Vittorio Crescenzi, Rome, all of (IT)

(73) Assignee: M.U.R.S.T. Italian Ministry for Universities and Scientific and Technological Research, Rome (IT)

( * ) Notice: Under 35 U.S.C. 154(b), the term of this patent shall be extended for 0 days.

(21) Appl. No.: 08/978,145

(22) Filed: Nov. 25, 1997

Related U.S. Application Data

(63) Continuation of application No. 08/367,318, filed on Mar. 30, 1995, now abandoned.

(30) Foreign Application Priority Data

Jul. 30, 1992 (IT) .............................................. PD92A0142

(51) Int. Cl.[7] .............................. A61F 5/14; A01N 43/04; A61K 31/715; C08B 37/00
(52) U.S. Cl. ........................ 536/123.1; 128/604; 514/54; 536/126
(58) Field of Search ..................................... 424/485, 486, 424/488; 426/531; 604/358; 536/123.1, 126; 514/54; 128/604

(56) References Cited

U.S. PATENT DOCUMENTS 5,277,915 * 1/1994 Provonchee et al. ................ 424/485

FOREIGN PATENT DOCUMENTS

0341745 * 5/1989 (EP) .
0518710A1 * 12/1992 (EP) .

OTHER PUBLICATIONS

Kuo et al., CA 106(3) :18968p, Jan. 1987.
Crescenzi et al., CA118(18) :175696p, May 1993.
Crescenzi et al., CA117(17) :171871v, Oct. 1992.
H. Rehm et al., *Biotechnology*, vol. 3, p. 560, 1983.

* cited by examiner

Primary Examiner—Thurman K. Page
Assistant Examiner—Sharon Howard
(74) Attorney, Agent, or Firm—Birch, Stewart, Kolasch & Birch, LLP

(57) ABSTRACT

The present invention is drawn to inner esters of gellan, wherein the carboxy groups are esterified with hydroxy groups from either the same or different molecules of gellan. The present invention is further drawn to methods of using the present inner esters of gellan in the fields of cosmetics, pharmaceuticals and in sanitary and surgical articles. The present invention is further drawn to products made from inner esters of gellan and to be used in the indicated fields.

21 Claims, No Drawings

AUTO-CROSS-LINKED GELLAN GUM

This application is a continuation of application Ser. No. 08/367,318 filed on Mar. 30, 1995, now abandoned.

BRIEF DESCRIPTION OF THE INVENTION

The present invention relates to intra- and/or intermolecular esters of the acidic polysaccharide gellan containing carboxy functions (glycuronan), wherein part of or all such functions are intraesterified with the hydroxy groups of the same gellan molecule, and, in addition, can be further interesterified with the hydroxy group of a different gellan molecule, thus forming intra/intermolecular lactonic or ester bonds. Intramolecular and intermolecular esters will be commonly defined as "inner esters". These inner esters of glycuronanes, wherein no hydroxy groups of other alcohols intervene, can also be defined as "auto-cross-lined polysaccharides". In the present specification, both terms will be used to define the new compounds of the present invention. The term "auto-cross-linked" refers to bridge links between the carboxy groups and hydroxy groups within the polysaccharide chain. Said inner esterification leads to the formation of a macromolecular network.

Depending on whether all or only some of the carboxy functions are esterified in the above manner, the new inner esters may be totally or partially esterified, i.e. total or partial esters. In the partial inner esters the remaining carboxy groups may be totally or partially esterified with the same or different monovalent or polyvalent alcohols, thus forming "outer" ester groups and, in the partial esters of both ester families, (i.e. both inner and outer esters) the non-esterified carboxy functions can be free or salified with pharmaceutically accepted metals or organic base counterions, which salts form part of the invention. The terms "polymeric gellan esters" and "polymers of gellan" used in the present invention designate auto-cross-linked gellan esters, both totally and partially inner esterified, and outer esters formed totally or partially on the remaining carboxy groups and pharmaceutically acceptable salts thereof.

Esterification between different gellan molecules (intermolecular esterification) results in an increase in the molecular weight of the product, the extent of which depends on and is proportional to the number of chains involved in auto-cross-linking. Lactone formation, on the other hand, if not accompanied by inter-chain linkage formation, would not result in a detectable change in molecular weight. The degree of cross-linking varies according to the conditions used in the preparation procedure which will be described hereinafter, especially the temperature and duration of the reaction. These conditions are described in the illustrative Examples which follow. The preparation procedures of the invention lad to a variety of products whose properties may range from water soluble viscous products in which only a limited number of glycuronan chains have been cross-linked (for example, 3–5, on the average, thus exhibiting average molecular weights approximately 3–5 times larger than the original glycuronan), to insoluble products (macromolecular networks or "hydrogels", i.e., hydrophilic gels) that can swell on contact with aqueous media to an extent which is mainly dependent on the degree of auto-cross-linking.

One embodiment of the invention is directed to the use of new inner esters of gellan, in particular, but not exclusively, of gellan based macromolecular networks ("hydrogels"), for instance in the sector of biodegradable plastic materials, for the manufacture of sanitary and surgical articles, in the cosmetic and pharmaceutical fields, in the food industry and in many other areas.

BACKGROUND OF THE INVENTION

Gellan is a gum consisting of an exocellular, microbial polysaccharide, produced from *Pseudomonas elodea* cell lines, composed of repeating tetrasaccharide units with the following structure:

-3-β-D-glcp-(1-4)-β-D-glcpA-1-4)-β-D-glcp-(1-4)-α-L-rhamp-(1- wherein "glcp" designates glucose, "glcpA" designates glucuronic acid, and "rhamp" designates rhamnose.

In its natural form, gellan gum contains an O-acetyl group at position C(6) of the first glcp residue and an O-glyceric group at position C(2) of the same residue. Natural gellan gum forms viscous solutions that can form fragile and heat-sensitive gels upon the addition of a salt, in particular, with bivalent cation salts such as $Ca^{2+}$ and $Mg^{2+}$ salts.

Deacylation of natural gellan leads to an improved gelling agent, currently sold under the name of "Gelrite®" for formulations in the alimentary field. In the presence of aqueous solutions of $MgCl_2$ or $CaCl_2$ (approximately 0.1% w/v salt and 0.8–1% w/v polysaccharide) Gelrite®0 forms highly resistant gels, that remain stable after autoclaving, are chemically inert and generally resistant to enzymatic digestion. Gellan is useful because of the ability of gellan chains to undergo a salt-inducted coil→double helix conformational change in water at room temperature. At higher ionic strengths, double helical sections form salt-stabilized partial aggregates which, eventually, constitute the "junction-zones" of the final aqueous gel state. The stability of the ordered double helical chain state as well as of the gel state depend on the nature of gellan counterions, since they influence the stability of the double-helix polysaccharide. It is to be expected that alteration of the charge density of the gellan chains by partial esterification of the carboxy groups may notably influence the polymer's properties in solution, producing derivatives with new gelling properties.

Auto-cross-linked esters of other polysaccharides are known (see European Patent Publication No. 0341745), but not auto-cross-linked esters of gellan. (Italian Patent Application No. PD91A000033 discloses outer esters of Gellan, but not auto-cross-linked esters of gellan).

DETAILED DESCRIPTION OF THE INVENTION

The auto-cross-linked gellans of the present invention can have all or only some of their carboxy functions in the form of inner esters.

The polymeric gellan esters can be totally auto-cross-linked, that is, there are no carboxy groups which are not inner-esterified. Another possibility is that the auto-cross-linking is only partial, that is, there are carboxy groups which can be totally or partially esterified with another alcohol component than from the polysaccharide itself. Outer esterification may be used to vary the hydrophilic/hydrophobic character of the resulting products by esterifying some or all of the carboxy groups not engaged in inner ester formation with hydrophilic alcohols (e.g. oligomeric monofunctional ethylene glycols) or hydrophobic alcohols (e.g. benzyl alcohol). This could alter the interactions between the solvents or their mixtures, revealing also further interactions with substances of various origin, including protein or chemical origin. To these ends, for the preparation of the new gellan derivatives for industrial purposes, the esterification method used is significant because of its yield and moderate reaction conditions. It is in fact possible to obtain new gellan products with the desired degree of esterification without degrading the polymer backbone. This esterification process is aimed at the uronic acid residues present in the polysaccharide.

When only a part of the carboxy groups are involved in auto-cross-linking, the degree of auto-cross-linking can be up to 95%, preferably between 1% and 60%, e.g. between 15% and 30%.

When the gellan is only partially esterified by auto-cross-linking, the remaining carboxy groups may be totally or partially esterified with mono- or polyvalent alcohols. Such alcohols can be selected from the group consisting of aliphatic, araliphatic, cycloaliphatic or heterocyclic alcohols, all of which can have up to 34 carbon atoms and may be saturated or unsaturated, and the carbon chain of which can be straight or branched. It is preferred that aliphatic alcohols have a maximum number of 12, preferably 6, carbon atoms. Araliphatic alcohols are preferably alcohols with one phenyl group and an aliphatic carbon chain of maximum 6 carbon atoms; an example is benzyl alcohol. Cycloaliphatic alcohols are derived from mono- or polycyclic hydrocarbons, and the rings contain between 5 and 7 carbon atoms.

In the polymeric gellan esters described above in which some carboxy groups remain free, these can be salified with metals or with organic bases, for example with alkaline or alkaline earth metals, such as sodium, potassium or calcium, or with ammonia or nitrogenous organic bases.

A group of polymeric gellan esters according to the present invention, useful in different industrial sectors as mentioned above, and this is, for example, in the food, paper, textile, and printing industries, and in the preparation of sanitary, medical-surgical, detergent and household articles, is represented by those in which the properties of the gellan component are to be exploited.

The specific use of these new esters can be seen in relation to the overall degree of esterification, inner or possible outer, or rather the number of esterified carboxy functions, with the number of salified groups and also the degree of cross-linking of the chain involved in the esterification. These are the factors which determine the solubility of the product and its visco-elastic properties. Thus, for example, the esters are highly expandable in aqueous liquids and their molecular structure makes them very suitable for use in the manufacture of plastic materials and as additives for such materials also in the form of hydrogels, membranes, sponges and non-woven tissues. These esters with high and low degrees of esterification and the salts thereof with inorganic or organic bases present different degrees of solubility in an aqueous environment and are therefore suitable for the preparation of gels and hydrogels which can be put to many uses, in cosmetics and in pharmaceuticals, in the medical-sanitary art, in foodstuffs and in agriculture in general.

An especially interesting aspect of the present invention is the use of the novel polymeric gellan esters as vehicles for pharmaceutically active substances, especially substances with topical, oral, rectal or ocular action, but also for parenteral use. The present invention, therefore, is also directed to these new uses and the respective products, and preferably to the pharmaceutical preparations containing the polymeric gellan esters of the present invention as a vehicle for active substances.

Hence, one aspect of the invention is directed to medicaments containing a) a pharmacologically active substance or an association of pharmacologically active substances; and b) a carrying vehicle constituted by an auto-cross-linked polymer of gellan as defined above. In the medicaments, component b) is an auto-cross-linked polymer of gellan gum, which may be expandable in an aqueous environment. Specific examples of medicaments are those wherein component a) is an anesthetic, analgesic or anti-inflammatory agent, a vasoconstrictor, an antibiotic/antibacterial, an antiviral or an antifungal agent. An interesting example of a medicament is one in which component a) is a proteinic agent. Examples of proteinic agents are enzymes such as chymotrypsin, streptokinase, lysozyme chloride, seaprose, serrapeptase, pronase, bromelains, montease and the like. In a subgroup of medicaments, component a) is a substance for oral, topical or local use.

It is also possible to formulate pharmaceutical preparations containing, as active ingredient, a polymeric auto-cross-linked gellan as defined above, together with an excipient. Excipients may be selected from the group of excipients normally used in the formulation of pharmaceutical preparations.

The pharmaceutical preparations according to the invention may be used in amounts corresponding to the usual amounts administered of the actual active ingredients, and they may be administered to patients in need therefor.

The low level of toxicity of the polymeric esters gellan according to the present invention can be utilized mainly in the pharmaceutical, cosmetic, sanitary-surgical and agro-alimentary fields, where the new gellan esters can be used as biodegradable plastic materials with various functions as needed and described below. Thus, for example, the gellan esters can also be used as additives for a wide variety of polymeric materials used for sanitary and surgical articles, such as polyurethanes, polyesters, polyolefins, polyamides, polysiloxanes, vinylic and acrylic polymers with the effect of increasing the biocompatibility of these materials.

In the cosmetic and pharmaceutical fields the polymeric gellan esters of the invention can be used to prepare ointments, creams and other types of medicaments for topical application or cosmetic products, such as sunshield creams, where they serve as stabilizers and emulsifying agents. In pharmaceuticals they can be used to the same advantage as disintegrating agents or as binding agents for tablets. According to a particularly important aspect of the present invention, the polymeric gellan esters are useful as a vehicle for pharmacologically active substances, especially those for topical or ocular application.

In the cosmetic articles according to the invention the polymeric gellan esters and their salts are mixed with the excipients commonly used in the art. Most used are creams, ointments, lotions for topical use in which the polymeric gellan ester or one of its salts can constitute the active cosmetic principle possibly with the addition of other cosmetically active principles, such as steroids, for example pregnenolone. The polymeric gellan ester can be partially auto-cross-linked, and the remaining carboxy groups can be partially or totally esterified with an alcohol with cosmetic action, such as dexpanthenol, or with an alcohol with no cosmetic action, such as a lower aliphatic alcohol. The effect of the cosmetic preparations is due to the intrinsic cosmetic properties of the polysaccharide component, as in the case of free gellan or its salts. The cosmetic articles can however be based on various other active principles, for example, desinfectants or sunshields or waterproofing or regenerating agents or antiwrinkle substances, or scented substances, especially perfumes.

An important application of the present invention concerns sanitary and surgical articles, methods for their manufacture and their use. The invention therefore encompasses all sanitary articles similar to those already on the market but containing a polymeric gellan ester or one of its salts, for example inserts or ophthalmic lenses.

Surgical and sanitary articles, according to the present invention, are presented by the polymeric gellan esters obtained as such from appropriate organic solutions and which can be made into woven or non-woven tissues, sheet and thread forms, thus obtaining films, sheets or gauzes for use in surgery, as auxiliaries and substitutes for the skin in sever cases of damage to this organ, such as burns, or as suture threads in surgical operations or for use in sanitary articles. The invention includes, in particular, such uses and a process for the preparation of such articles which comprises the formation of a solution of a polymeric gellan ester or of one of its salts in a suitable organic solvent, for example a ketone. The organic solvent can also be an organic sulfoxide, that is, a dialkylsulfoxide with alkyl group with between 1 to 6 carbon atoms, such as dimethylsulfoxide or diethylsulfoxide. The organic solvent can also be a fluorinated solvent with a low boiling point, such as hexafluoroisopropanol. The solution obtained is then exposed to a rolling or spinning process to remove the organic solvent by contact with another organic or aqueous solvent which can be mixed with the first solvent in which the polymeric gellan ester is not soluble, especially lower aliphatic alcohol, for example ethyl alcohol (wet spinning). If a solvent with a sufficiently low boiling point is used to prepare the solution of the gellan derivative, removing said solvent in dry conditions is accomplished with a gas current, especially suitably heated nitrogen (dry spinning). Excellent results are also obtained with dry-wet spinning.

The threads obtained with the polymeric gellan esters can be used to prepare gauzes to be used in the medication of wounds and in surgery. The use of such gauzes offers the extraordinary advantage in that they are biodegradable in the organism, depending on the degree of auto-cross-linking.

When preparing said sanitary and surgical articles, suitable plastifying materials can be added to improve their mechanical characteristics, such as in the case of threads, to improve their resistance to knots. Such plastifying agents can be, for example, alkaline salts of fatty acids, for example sodium stearate or sodium palmitate, and esters of organic acids with a large number of carbon atoms, etc.

Sanitary and surgical articles made with the polymeric gellan esters according to the invention can be in the form of microspheres or microgranules.

Another application of the new polymeric gellan esters where their biotolerability is exploited, is represented by the preparation of capsules or microgranules for subcutaneous implant of medicaments or microcapsules for injection, for example by subcutaneous or intramuscular route.

Of great importance is also the preparation of microcapsules containing polymeric gellan esters. This preparation method opens up a vast field of application where a retard effect is desired following injection.

Another medical-surgical application of the gellan esters is represented by the preparation of a side variety of solid inserts such as plates, disks, sheets, etc., substituting those currently in use and made of metal or synthetic plastic material, where such inserts are intended to be removed after a certain period. Preparations made of animal collagen, being of a proteic nature, often cause unpleasant side effects such as inflammation or rejection phenomena. In the case of gellan esters this danger does not exist.

Also included in the application of the gellan esters, according to the present invention, in the medical-surgical field, are preparations of expandable material especially in the form of sponges, for the medication of various kinds of wounds or lesions.

Another application of the gellan esters is in the alimentary field. The esters can be used in foodstuffs for the preservation of foods. They can be in the form of a film or wrapping protecting the alimentary articles.

Hence, a further aspect of the invention relates to alimentary articles containing an inner ester according to the invention together with the food component.

Still another aspect of the invention is directed to the use of the esters of gellan, whether they are totally or partially inner esterified or, if partially inner esterified, also totally or partially esterified with other alcohols on free carboxy groups, and, if still partially esterified, also salts of said esters, in the coloring and household manufacturing industries. For these purposes the resistance against atmospheric influence provided by the esters is utilized.

A special advantage connected to the gellan esters is their biodegradability by the environment, and their biotolerability. The gellan esters are biocompatible with the human organism but not degradable by it.

According to the invention, the inner esters are prepared from gellan which most often is obtained in the form of a sodium salt. The sodium salt is converted into a quaternary ammonium salt, preferably a quaternary alkyl ammonium salt such as a tetrabutyl ammonium salt of gellan. The conversion into a quaternary ammonium salt an be performed by reacting the sodium salt with a resin salified with the quaternary ammonium base. By treating the quaternary ammonium salt of gellan solubilized in an aprotic solvent such as dimethyl sulfoxide (DMSO) with an organic base such as pyridine or a resin such as Amberlite LA-Z liquid resin which will block the acid prepared during the esterification and subsequent treating the obtained solution with an agent which promotes the formation of an ester such as 2-chloro-1-methylpyridinium iodide. The 2-chloro-1-methylpyridinium iodide is dissolved in an aprotic solvent such as DMSO and is added slowly to the pyridine containing solution of the quaternary ammonium salt. The molar ratio between the quaternary ammonium salt of gellan, pyridine and 2-chloro-1-methylpyridinium iodide determines stoichiometrically the degree of inner esterification. Upon completion of the esterification a solution of a salt such as NaBr is added to the inner ester in order to convert the remaining free carboxylate groups into sodium salt form. The final solution of the inner ester is then precipitated by being poured slowly into a non-aqueous liquid such as absolute ethanol. Finally, the precipitate formed may be washed with aqueous and non-aqueous liquids in turn and finally dried.

For the preparation of a film of inner ester of gellan a film of quaternary ammonium salt of gellan may be immersed in a liquid in which it is insoluble, e.g. methylene chloride. Ester formation promotion agents such as 2-chloro-1-methylpyridiniumiodide are then added to the gellan salt and the reactants are allowed to react. After completed esterification the inner ester product may be converted into a salt, if desired and washed and dried. Hydrogels are formed in the same manner as are films, only in the form of beads instead of film. When outer esters of gellan are to be prepared, the outer esterification takes place before the inner esterification is performed. The salification of the inner esters may be performed with inorganic or organic bases. Examples of inorganic salts are the alkali metal salts such as sodium and potassium salts and earth alkali-metal salts such as calcium and magnesium salts. Also ammonium salts may be prepared. When the salts are to be used in the alimentary or pharmaceutical field they must of course be alimentary or pharmaceutically tolerable. Non-tolerable salts may, however, be used in e.g. purification steps, provided that the non-tolerable salt moieties are removed and replaced by tolerable moieties. Salts with organic bases are preferably salts with amines which can be derived from aliphatic, araliphatic, cycloaliphatic or heterocyclic amines.

The present invention also includes modifications in the preparation procedures of the new auto-cross-linked gellan products, wherein a procedure is introduced at any one stage or is begun at an intermediate stage and the remaining steps are performed, or the starting products are formed by synthesis.

The invention is illustrated by the following examples, but is not in any way limited by the same.

EXAMPLE 1

Preparation of the Tetrabutylammonium Salt of Gellan Gum 10 g of gellan sodium salt ("Gelrite") are dissolves overnight in 400 ml of water under stirring.

Separately, 40 ml of a Dowex® M15 resin in H+ form are placed in a 250-ml Erlenmeyer flask and washed with $H_2O$ until a pH of about 7 is reached.

A 1M solution of tetrabutylammonium hydroxide is added to transform the resin into TBA+ form.

It is then washed with $H_2O$ until a pH of about 7 is reached.

The temperature of the gellan solution is reduced to 8° C. in a cryostat and the resin is added under gentle shaking; the resulting mixture is left to stand at room temperature for 24–36 hours.

The solution thus obtained is very viscous and difficult to filter.

It is centrifugated at 11,000 r.p.m. for 30 minutes after which the liquid upper phase is removed and used as such or freeze-dried.

EXAMPLE 2

Preparation of Auto-Cross-Linked Gellan with 25% of the Carboxy Groups Involved in the Inner Esterification 8.9 g of the tetrabutylammonium salt of gellan, with a molecular weight of 700,000, corresponding to 10 mEq of the monomeric unit, are dissolved in DMSO at 25° C. to a concentration of 25 mg/ml (356 ml in all).

Once solubilization is complete, 2.5 mEq of pyridine (0.198 g) are added and this is shaken for at least 30 minutes.

A solution of 2.5 mEq (0.639 g) of 2-chloro-1-methylpyridinium iodide in 60 ml of DMSO is slowly added drop by drop and the resulting mixture is shaken for 15 hours at a constant temperature of 30° C.

20 ml of a 30% solution of NaBr in $H_2O$ is then added.

The final solution is slowly dripped into 1400 ml of absolute ethanol while being continuously shaken.

A precipitate is thus formed which is filtered and washed:
3 times with 150 ml of a mixture of ethanol/$H_2O$ 90/10
3 times with 150 ml of absolute ethanol
twice with 150 ml of acetone The precipitate is then vacuum dried for at least 24 hours at room temperature.

6.6 g of the title product are obtained.

Quantitative determination of the ester groups is performed by the saponification method described on pages 169–172 of "Quantitative organic analysis via functional groups" 4th Edition, John Wiley and Sons Publication (1979).

EXAMPLE 3

Preparation of Auto-Cross-Linked Gellan with 50% of the Carboxy Groups Involved in the Inner Esterification 8.9 g of the tetrabutylammonium salt of gellan, with a molecular weight of 700,000, corresponding to 10 mEq of the monomeric unit, are dissolved in DMSO at 25° C. to a concentration of 25 mg/ml (356 ml in all).

Once solubilization is complete, 5.0 mEq of pyridine are added (0.396 g) and this is shaken for at least 30 minutes.

A solution of 5.0 mEq (1.28 g) of 2-chloro-1-methylpyridinium iodide in 60 ml of DMSO is slowly added drop by drop and the resulting mixture is shaken for 15 hours at a constant temperature of 30° C.

20 ml of a 30% solution of NaBr in $H_2O$ are then added.

The final solution is slowly dripped into 1400 ml of absolute ethanol while being continuously shaken.

A precipitate is thus obtained which is filtered and washed:
3 times with 150 ml of a mixture of ethanol/$H_2O$ 90/10
3 times with 150 ml of absolute ethanol
3 times with 150 ml of acetone The precipitate is then vacuum dried for at least 24 hours at room temperature.

6.5 g of the title product was thus obtained.

Quantitative determination of the ester groups is performed by the saponification method described on pages 168–172 of "Quantitative organic analysis via functional groups" 4th Edition, John Wiley and Sons Publication (1979).

EXAMPLE 4

Preparation of Auto-Cross-Linked Gellan with 75% of the Carboxy Groups Involved in the Inner Esterification 8.9 g of the tetrabutylammonium salt of gellan gum, with a molecular weight of 700,000, corresponding to 10 mEq of the monomeric unit, are dissolved in DMSO at 25° C. to a concentration of 25 mg/ml (356 ml in all).

Once solubilization is complete, 7.5 mEq of pyridine are added (0.594 g) and this is shaken for at least 30 minutes.

A solution of 7.5 mEq (1.92 g) of 2-chloro-1-methylpyridinium iodide is slowly dripped into 60 ml of DMSO and the resulting mixture is shaken for 15 hours at a constant temperature of 30° C.

20 ml of a 30% solution of NaBr in $H_2O$ are then added.

The final solution is slowly added drop by drop to 1400 of absolute ethanol while being constantly shaken.

A precipitate is obtained which is filtered and washed:
3 times with 150 ml of a mixture of ethanol/$H_2O$ 90/10
3 times with 150 ml of absolute ethanol
3 times with 150 ml of acetone The precipitate is then vacuum dried for at least 24 hours at room temperature.

6.4 g of the title product are thus obtained.

Quantitative determination of the ester groups is performed by the saponification method described on pages 169–172 of "Quantitative organic analysis via functional groups" 4th Edition, John Wiley and Sons Publication (1979).

EXAMPLE 5

Preparation of Auto-Cross-Linked Gellan with 100% of the Carboxy Groups Involved in the Inner Esterification 8.9 g of the tetrabutylammonium salt of gellan, with a molecular weight of 700,000, corresponding to 10 mEq of the monomeric unit, are dissolved in DMSO at 25° C. to a concentration of 25 mg/ml (356 ml in all).

Once solubilization is complete, 10 mEq of pyridine (0.792 g) are added and this is shaken for at least 30 minutes.

A solution of 10 mEq (2.56 g) of 2-chloro-1-methylpyridinium iodide are slowly dripped into 60 ml of DMSO and the resulting mixture is shaken for 15 hours at a constant temperature of 30° C.

The solution is slowly added drop by drop to 1400 ml of absolute ethanol while being continuously shaken.

A precipitate is obtained which is filtered and washed:

3 times with 150 ml of a mixture of ethanol/$H_2O$ 90.10

3 times with 150 ml of absolute ethanol twice with 150 ml of acetone

The precipitate is then vacuum dried for at least 24 hours at room temperature.

6.29 g of the title product are thus obtained.

Quantitative determination of the ester groups is performed by the saponification method described on pages 169–172 of "Quantitative organic analysis via functional groups" 4th Edition, John Wiley and Sons Publication (1979).

EXAMPLE 6

Preparation of the Partial Benzyl Ester of Auto-Cross-Linked Gellan 8.9 g of the Tetrabutylammonium salt of gellan, with a molecular weight of 700,000, corresponding to 10 mEq of the monomeric unit, are dissolved in DMSO at 25° C. to a concentration of 25 mg/ml (356 ml in all).

Once solubilization is complete, 2.5 mEq (0.428 g) of benzyl bromide are added and the solution is shaken for at least 15 hours at a temperature of 30° C.

2.5 mEq (0.198 g) of pyridine are then added and shaken for 30 minutes.

A solution of 2.5 mEq (0.639) of 2-chloro-1-methylpyridinium iodide is slowly added drop by drop to 60 ml of DMSO and the mixture is shaken for 15 hours at a constant temperature of 30° C.

20 ml of a 30% solution of NaBr in $H_2O$ are then added.

The solution is then slowly dripped into 1400 ml of absolute ethanol while being constantly shaken.

A precipitate is thus obtained which is filtered and washed:

3 times with 150 ml of a mixture of ethanol/$H_2O$ 90.10

3 times with 150 ml of absolute ethanol twice with 150 ml of acetone

The precipitate is then vacuum dried for at least 24 hours at room temperature.

6.7 g of the title product are thus obtained and it presents the following characteristics:

25% of the carboxy groups esterified with benzyl alcohol

25% of the carboxy groups involved in the inner esterification

50% of the carboxy groups salified with sodium.

Quantitative determination of the ester groups is performed by the saponification method described on pages 169–172 of "Quantitative organic analysis via functional groups" 4th Edition, John Wiley and Sons Publication (1979).

EXAMPLE 7

Preparation of an Auto-Cross-Linked Gellan Film 8.9 g of film obtained with the tetrabutylammonium salt of gellan with a molecular weight of 700,000, corresponding to 10 mEq of the monomeric unit, are immersed in 450 ml of methylene chloride and the reaction container is slowly rotated.

7.5 ml of Amberlite LA-2 liquid resin and 10 mEq (2.56 g) of 2-chloro-1-methyl-pyridinium iodide are added.

This mixture is slowly rotated for at least 48 hours in the dark and at room temperature.

At the end of the reaction the are immersed in a bath of ammonium acetate in $H_2O$ for at least 2 hours.

They are then immersed in a bath containing a 30% solution of NaBr in $H_2O$ and left for at least 2–3 hours. Finally, they are thoroughly washed in $H_2O$ until their conductivity values are very low.

The films are then vacuum dried for at least 24 hours at room temperature.

EXAMPLE 8

Preparation of Auto-Cross-Linked Gellan Hydrogels 8.9 g of freeze-dried beads of the tetrabutylammonium salt of gellan gum, with a molecular weight of 700,000, corresponding to 10 mEq of the monomeric unit are immersed in 450 l of methylene chloride and the reaction container is slowly rotated.

7.5 ml of Amberlite LA-2 liquid resin and 10 mEq (2.56 g) of 2-chloro-1-methyl-pyridinium iodide are added.

The mixture is slowly rotated in a dark place for at least 48 hours.

Once the reaction is complete the beads are immersed in a bath of ammonium acetate in $H_2O$ for at least 2 hours.

They are then immersed in a bath of a 30% solution of NaBr in $H_2O$ and left there for at least 2–3 hours. They are then thoroughly washed in $H_2O$ until their conductivity values are very low.

The beads are then vacuum dried for at least 24 hours at room temperature.

The invention being thus described, it is clear that these methods can be modified in various ways. Such modifications are not to be considered as divergences from the spirit and purposes of the invention and any modification which would be evident to an expert in the field comes within the scope of the following claims.

What is claimed is:

1. Polymers of gellan wherein said gellan is 1–15% auto-cross-linked by lactone bonds between carboxy and hydroxy groups of the same molecule or by ester bonds between carboxy groups and hydroxy groups of different molecules of the polysaccharide itself, and wherein remaining carboxy groups may be free or toally or partially esterified with mono or polyvalent alcohols, and pharmaceutically acceptable salts of any free carboxy groups with inorganic or organic bases.

2. Polymers of gellan according to claim 1, wherein only a part of the carboxy groups are involved in the auto-cross-linking process.

3. Polymers of partially auto-cross-linked gellan according to claim 1, wherein the remaining carboxy groups are totally or partially esterified with aliphatic, araliphatic, cycloaliphatic or heterocyclic alcohols.

4. Pharmaceutical preparations containing as active ingredient a polymer according to claim 1 together with an excipient.

5. Medicaments containing:
   a) a pharmacologically active substance or an association of pharmacologically active substances;
   b) a carrying vehicle constituted by an auto-cross-linked polymer of gellan according to claim 1.

6. Medicaments according to claim 5, wherein component a) is a substance for oral, topical or local use.

7. Medicaments according to claim 5, wherein component b) is an auto-cross-linked polymer of gellan gum, which is water-insoluble but swellable in water.

8. Medicaments according to claim 5 wherein component a) is an anesthetic, analgesic or anti-inflammatory agent, a vasoconstrictor, an antibiotic/antibacterial, an antiviral or an antifungal agent.

9. Medicaments according to claim 5 wherein component a) is a protein-derived agent.

10. Sanitary and surgical articles containing an auto-cross-linked gellan polymer according to claim 1.

11. Sanitary and surgical articles according to claim 10 in the form of threads, gauzes and films.

12. Sanitary and surgical articles according to claim 10 in the form of non-woven tissues.

13. Sanitary and surgical articles according to claim 10 in the form of microspheres or microgranules.

14. Sanitary and surgical articles according to claim 10 constituted by sponges.

15. Cosmetic articles containing an auto-cross-linked gellan polymer according to claim 1.

16. Alimentary articles containing an auto-cross-linked gellan polymer according to claim 1.

17. Alimentary articles according to claim 16 in the form of membranes for the preservation of food.

18. A procedure for the preparation of threads or films of auto-cross-linked gellan polymers having 1–15% auto-cross-linking, wherein said polymers are dissolved in a first organic solvent, the solution is made into sheet or thread form, and the first solvent is eliminated.

19. The procedure according to claim 18 wherein the elimination of the first organic solvent is performed by treatment with a second suitable organic or aqueous solvent which is soluble in the first solvent, and in which the polymers are not soluble, and said second solvent is removed from the polymers.

20. A procedure according to claim 19, wherein dimethylsulfoxide is used as the first solvent.

21. A procedure according to claim 19, wherein hexafluoroisopropanol is used as the first solvent, and said solvent is eliminated with a current of suitably heated inert gas.

* * * * *

UNITED STATES PATENT AND TRADEMARK OFFICE
CERTIFICATE OF CORRECTION

PATENT NO. : 6,172,219

DATED : January 9, 2001

INVENTOR(S) : Lanfranco Callegaro, et al.

It is certified that error appears in the above-identified patent and that said Letters Patent is hereby corrected as shown below:

In the section "Related U.S. Application Data" insert after "now abandoned" the following -- which is a 371 National application of PCT/EP93/02013, filed July 28, 1993--.

Signed and Sealed this

Eighth Day of May, 2001

*Attest:*

NICHOLAS P. GODICI

*Attesting Officer*   *Acting Director of the United States Patent and Trademark Office*